US00PP31229P3

(12) United States Plant Patent
Kunieda

(10) Patent No.: US PP31,229 P3
(45) Date of Patent: Dec. 17, 2019

(54) ***ROSA* L. PLANT NAMED '80103WABARA'**

(50) Latin Name: ***Rosa* L.**
Varietal Denomination: 80103WABARA

(71) Applicant: Rose Universe Co., Ltd., Shiga (JP)

(72) Inventor: Keiji Kunieda, Shiga (JP)

(73) Assignee: Rose University Co., Ltd., Shiga (JP)

( * ) Notice: Subject to any disclaimer, the term of this patent is extended or adjusted under 35 U.S.C. 154(b) by 0 days.

(21) Appl. No.: 15/932,569

(22) Filed: Mar. 15, 2018

(65) Prior Publication Data

US 2019/0239402 P1 Aug. 1, 2019

(30) Foreign Application Priority Data

Jan. 26, 2018 (JP) ..... PBR PVP 32809

(51) Int. Cl.
*A01H 5/02* (2018.01)
*A01H 6/74* (2018.01)

(52) U.S. Cl.
USPC ..... Plt./103
CPC ..... *A01H 6/749* (2018.05)

(58) Field of Classification Search
USPC ..... Plt./102, 103, 104
CPC ..... A01H 5/02; A01H 6/749
See application file for complete search history.

*Primary Examiner* — Keith O. Robinson
(74) *Attorney, Agent, or Firm* — Kilpatrick Townsend & Stockton LLP

(57) ABSTRACT

Described herein is a new and distinct rose plant named '80103WABARA' that has large, white, star-shaped flowers with dense petals. The variety is primarily used as a potted plant and for cut flowers.

4 Drawing Sheets

Genus and species: The rose variety of this invention is botanically identified as *Rosa* L.

Variety denomination: The variety denomination is '80103WABARA'.

CROSS-REFERENCES TO RELATED APPLICATIONS

This application claims priority to Japanese Plant Variety Protection Application No. 32809, filed Jan. 26, 2018.

BACKGROUND OF THE INVENTION

The present invention is a new and distinct variety of a *Rosa* L. rose plant obtained from a cross between maternal variety 'An' (unpatented) and an unnamed paternal variety of unknown parentage owned by the breeder. The cross was performed by hand pollination in May 2014 and seeds were planted in January 2015. '80103WABARA' was selected from the varieties that flowered in September 2017. Stable characteristics were confirmed following selection. The plant was asexually reproduced by grafting.

BRIEF SUMMARY OF THE INVENTION

'80103WABARA' is reproduced by grafting. '80103WABARA' can be distinguished from the maternal variety, 'An', by: (1) a large number of petals (128 petals compared to 54 for 'An'); (2) color grouping (white compared to pink blend for 'An'); (3) main color of the inner side of the petal (RHS 158D compared to RHS 49C for 'An'); and (4) petal secondary color (RHS 4D compared to absent for 'An'). '80103WABARA' is also distinguished from comparison variety 'Rikuhotaru' (unpatented) by the main color of the inner side of the petal (RHS 158D compared to RHS 13D for 'Rikuhotaru').

The variety '80103WABARA' is maintained at Shiga-ken Moryama-shi, 1465 Sugie-cho 524-0062, Japan and is maintained in soil cultivation. The variety is primarily used as a potted plant and for cut flowers. Planting in Japan is from mid-October to late December. Grafting is from late September to early October. The plant will flower annually when grown in a greenhouse. The plant can be grown at a temperature of 5° C. to 40° C.

BRIEF DESCRIPTION OF THE PHOTOGRAPHS

The accompanying photographs illustrate the appearance of the new *Rosa* L. variety. The plant depicted in the photographs is about two year in age. The colors in the photographs are depicted as nearly true as is reasonably possible to obtain in colored reproductions of this type. Colors in the photographs may differ slightly from the color values cited in the detailed botanical description.

Figure 1:
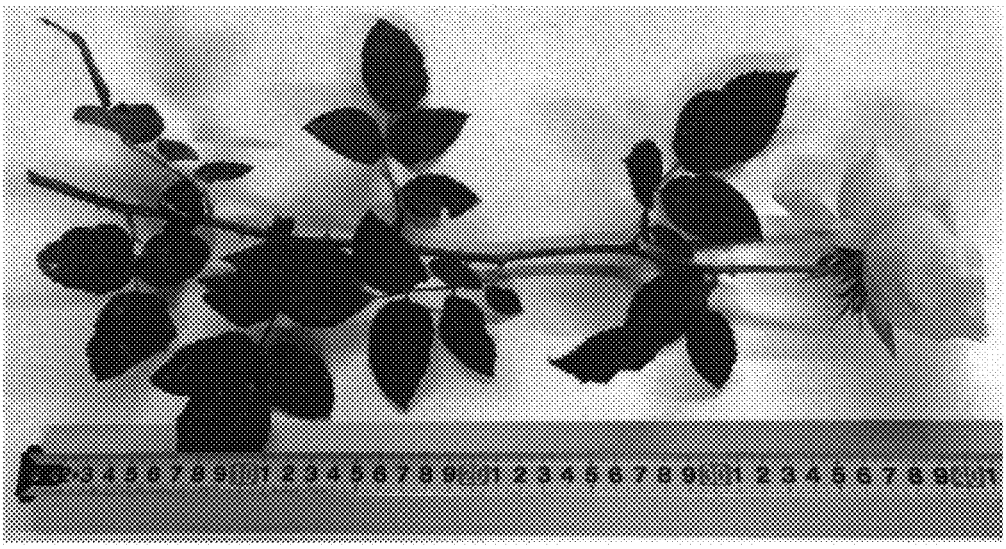
Figure 2:
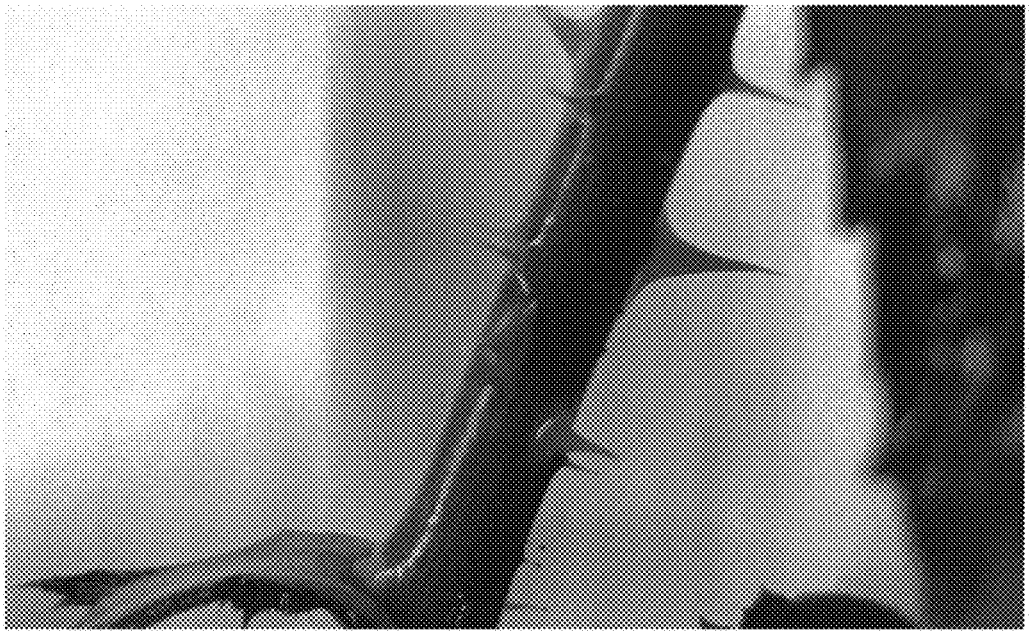
Figure 3:
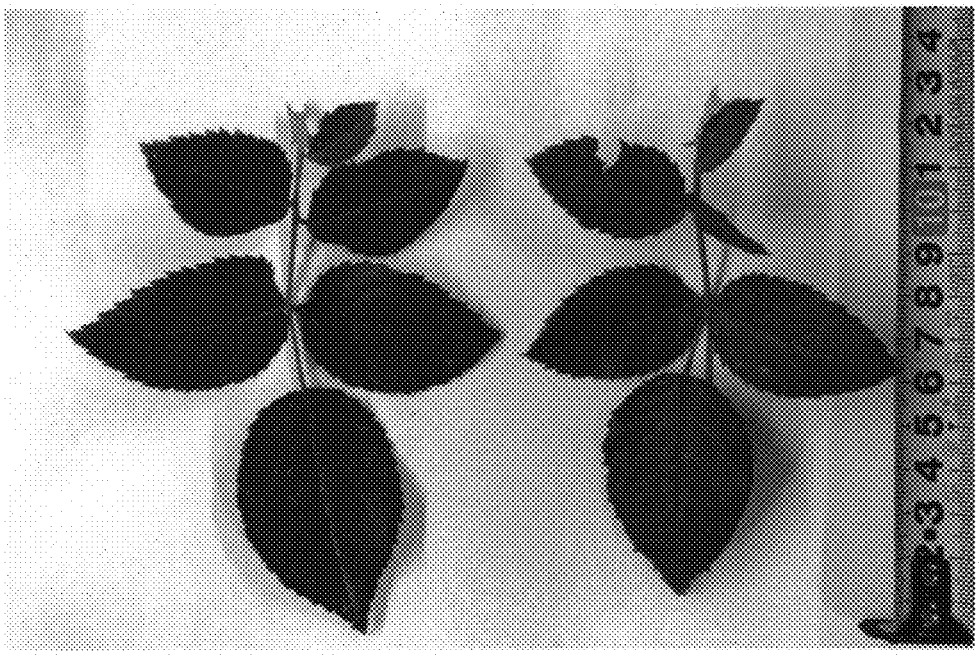
Figure 4:
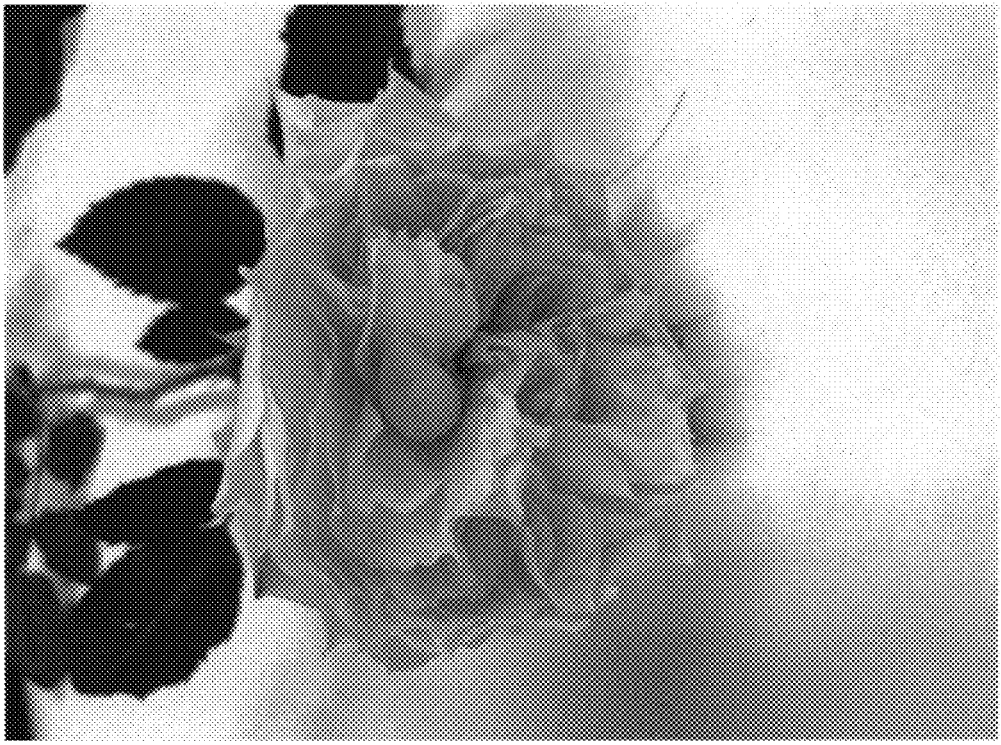
Figure 5:
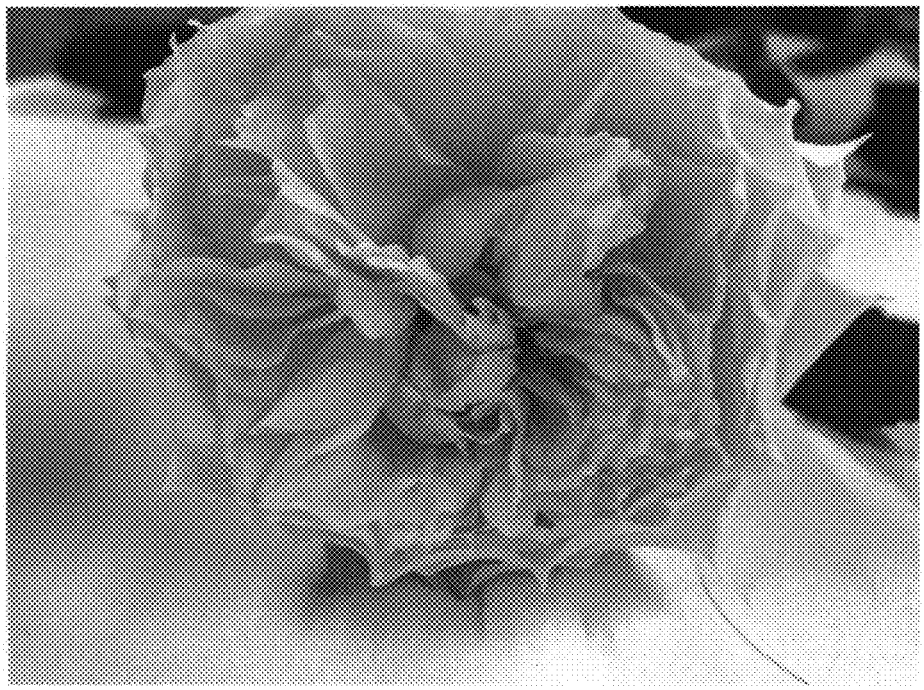
Figure 6:
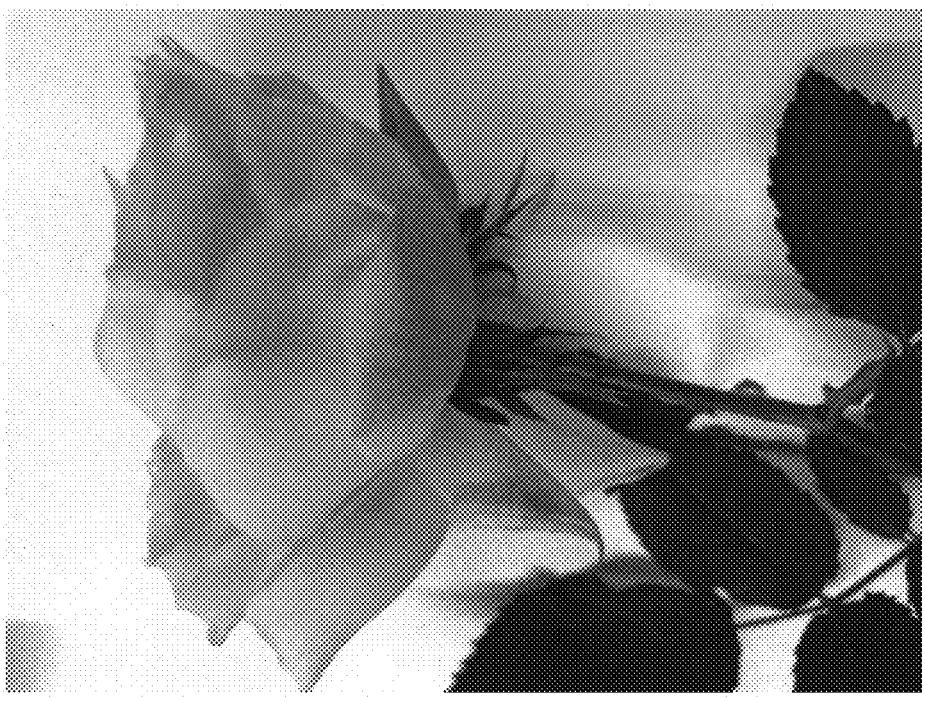
Figure 7:
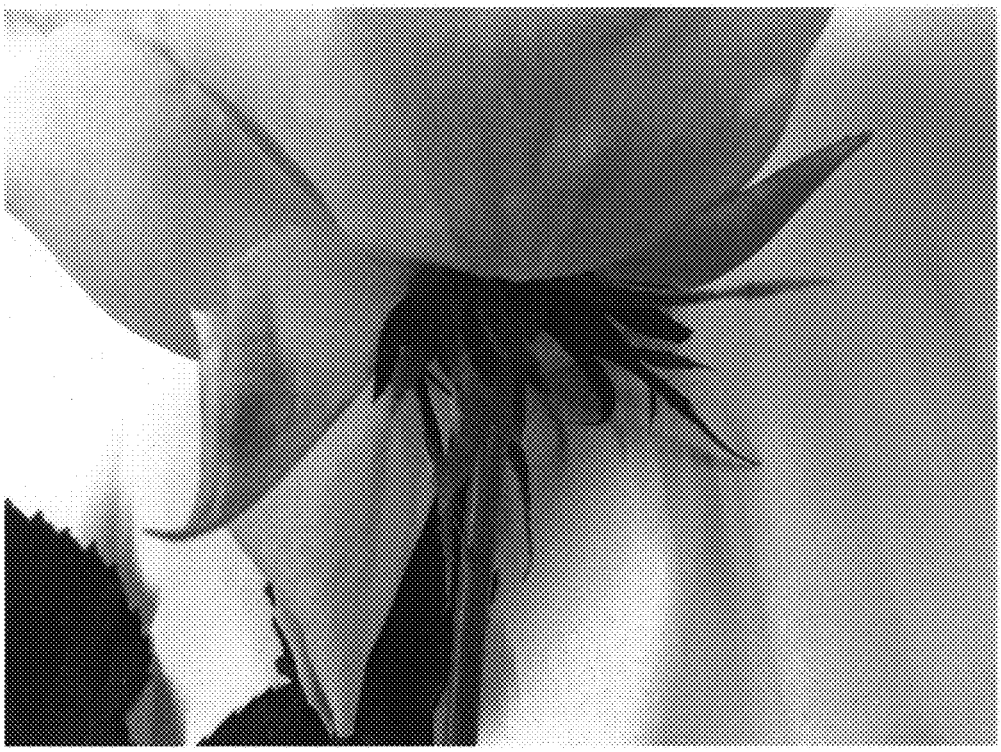
Figure 8:
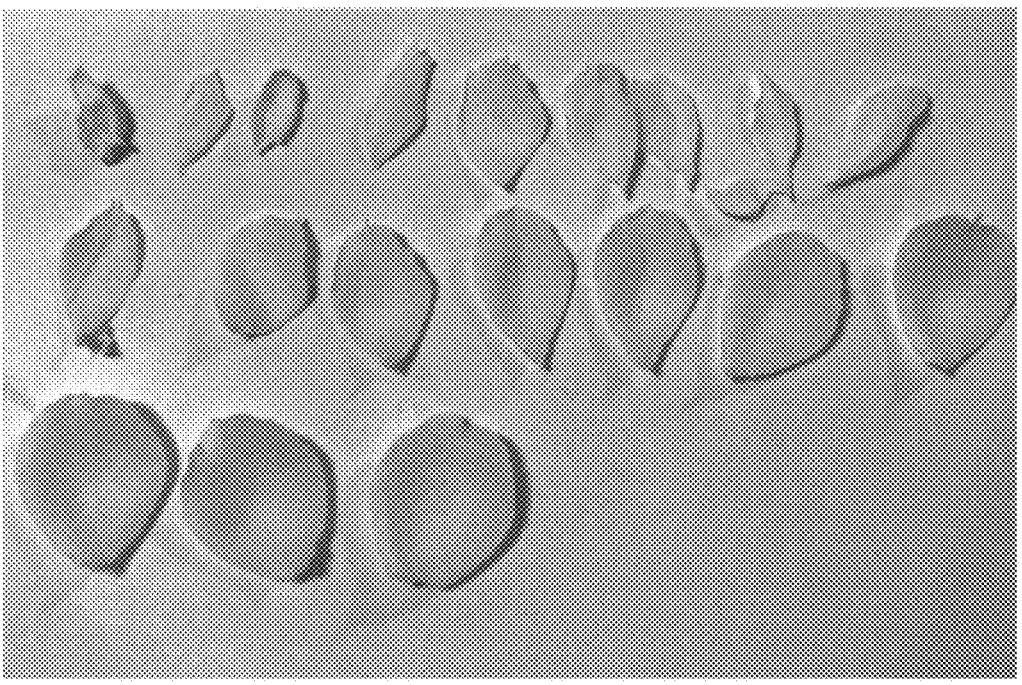

FIG. 1 shows a branch with a flower and leaves.
FIG. 2 shows the prickles on a branch.
FIG. 3 shows leaves with leaflets.
FIG. 4 shows a close-up side view of a flower.
FIG. 5 shows a close-up front view of a flower.
FIG. 6 shows sepals at the base of a flower.
FIG. 7 shows a close-up view of sepals at the base of a flower.
FIG. 8 shows individual petals.

DETAILED BOTANICAL DESCRIPTION

The following is a detailed description of '80103WABARA' with color descriptions based on The Royal Horticultural Society (R.H.S.) Colour Chart published 2015.

CHARACTERISTICS OF VARIETY

Plant:

*Growth type.*—Shrub.
*Growth habit.*—Semi-upright.

*Height.*—39.5 cm.
*Young shoot, anthocyanin coloration.*—Absent.
*Stem, number of prickles.*—50 to 80 per branch.
*Prickles, predominant color.*—167-A.

Leaf:
*Size.*—13 cm.
*Anthocyanin coloration.*—Absent.
*Glossiness of upper side.*—Weak.
*Leaflet, undulation of margin.*—Very weak.
*Terminal leaflet, blade shape.*—Medium Elliptic.
*Terminal leaflet shape of base of blade.*—Rounded.
*Terminal leaflet shape of apex of blade.*—Acuminate.

Flowers:
*Flowering shoot, flowering laterals.*—Present.
*Flowering shoot, number of flowering laterals.*—1 lateral.
*Flowering shoot, number of flowers.*—1 flower.
*Flowering shoot number of flowers per lateral.*—1 flower.
*Flower type.*—Double.
*Number of petals.*—128.
*Flower color.*—NN155-A.
*Density of petals (for double flowered variety).*—Dense (on a scale of very loose, loose, medium, or dense).
*Flower diameter.*—9 cm.
*Flower shape.*—Star-shaped.
*Profile of upper part of flower.*—Flat.
*Profile of lower part of flower.*—Flat.
*Reflexing of petals one-by-one.*—Absent.
*Petal shape.*—Elliptic.
*Petal incisions.*—Weak.
*Reflexing of petal margin.*—Very strong.
*Petal undulation.*—Very strong.
*Petal length.*—4 cm.
*Petal width.*—4 cm.
*Number of colors on inner side of petal.*—Two.
*Main color on inner side of petal.*—158B.
*Secondary color of petal.*—4D.
*Distribution of secondary color on inner side of petal.*—At base.
*Basal spot on the inner side of petal.*—Present.
*Color of basal spot on inner side of petal.*—NN155-A.
*Main color of petal on the outer side.*—67A.
*Outer stamen, predominant color of filament.*—157-C.
*Sepal, length.*—About 2.5 cm.
*Sepal, width.*—About 0.5 cm.
*Sepal, texture.*—Normal.
*Sepal, color.*—137-C.
*Sepal, shape.*—Absent or Medium extensions.
*Flower bud, length.*—1.5 to 2 cm.
*Flower bud, diameter.*—1 to 1.5 cm.
*Flower bud, shape.*—Sharp at the end.
*Flower bud, color.*—137-C.
*Receptacle, length.*—0.7 to 1.0 cm.
*Receptacle, width.*—0.7 to 1.0 cm.
*Receptacle texture.*—Normal.
*Receptacle color.*—137-C.
*Pollen color.*—15-A.
*Anthers, length.*—0.15 cm.
*Anthers, color.*—15-A.
*Anthers, quantity.*—20 to 30.
*Filament, length.*—0.4 to 0.6 cm.
*Pistil, length.*—0.4 to 0.6 cm.
*Pistil, number.*—Fewer than 10.
*Stigma, color.*—17-D.
*Stigma shape.*—Crescent.
*Hips.*—Absent.
*Petiole, length.*—2 to 3 cm.
*Petiole, diameter.*—0.1 to 0.2 cm.
*Petiole, color.*—146-B.
*Rachies, length.*—5 to 7 cm.

Disease resistance/susceptibility: There is no specific disease or pest to which the plant is resistant or susceptible.

What is claimed is:

1. A new and distinct variety of a *Rosa* L. rose plant having the characteristics substantially as described and illustrated herein.

* * * * *